(12) United States Patent
Fischer et al.

(10) Patent No.: US 6,957,907 B2
(45) Date of Patent: Oct. 25, 2005

(54) ILLUMINATION APPARATUS HAVING A LIGHT-CONVERTING LENS FOR INCREASING VISUAL CONTRAST BETWEEN DIFFERENT ORAL TISSUES

(75) Inventors: Dan E. Fischer, Sandy, UT (US); Vasiliy Nosov, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 103 days.

(21) Appl. No.: 10/411,913

(22) Filed: Apr. 11, 2003

(65) Prior Publication Data

US 2004/0201980 A1 Oct. 14, 2004

(51) Int. Cl.$^7$ .............................................. A61B 1/24
(52) U.S. Cl. ........................... 362/573; 362/2; 362/16; 362/583; 433/29
(58) Field of Search ................................ 362/573, 583, 362/551, 553, 555, 572, 109, 119, 259, 317, 326, 351, 257, 293, 2, 16, 84, 260; 359/355, 326, 350; 385/115, 116, 119; 433/29, 25

(56) References Cited

U.S. PATENT DOCUMENTS

| | | | | |
|---|---|---|---|---|
| 1,706,161 A | * | 3/1929 | Hollnagel ................... 607/93 |
| 2,420,307 A | * | 5/1947 | Fristoe ....................... 340/321 |
| 3,261,978 A | * | 7/1966 | Brenman ..................... 15/105 |
| 4,266,535 A | | 5/1981 | Moret |
| 4,522,594 A | | 6/1985 | Stark et al. |
| 4,530,039 A | * | 7/1985 | Shin-Shi ..................... 362/158 |
| 4,611,992 A | | 9/1986 | Lokken |
| 4,666,405 A | | 5/1987 | Ericson |
| 4,666,406 A | * | 5/1987 | Kanca, III ................... 433/229 |
| 4,716,501 A | * | 12/1987 | McKee et al. ............... 362/31 |
| 5,014,171 A | * | 5/1991 | Price, III ..................... 362/277 |
| 5,021,931 A | * | 6/1991 | Matsui et al. ................ 362/84 |
| 5,169,228 A | * | 12/1992 | Breitzler ..................... 362/293 |
| 5,288,231 A | | 2/1994 | Kuehn et al. |
| 5,415,543 A | * | 5/1995 | Rozmajzl, Jr. ............... 433/29 |
| 5,420,768 A | * | 5/1995 | Kennedy ..................... 362/119 |
| 5,448,323 A | | 9/1995 | Clark et al. |
| 5,527,261 A | | 6/1996 | Monroe et al. |
| 5,634,711 A | * | 6/1997 | Kennedy et al. ............. 362/119 |
| 5,733,029 A | | 3/1998 | Monroe |
| 5,749,724 A | | 5/1998 | Cheng |
| 5,762,605 A | | 6/1998 | Cane et al. |
| 5,791,898 A | | 8/1998 | Maissami |
| 5,905,268 A | | 5/1999 | Garcia et al. |
| 5,912,470 A | * | 6/1999 | Eibofner et al. ........... 250/504 H |
| 6,113,281 A | * | 9/2000 | Davis ......................... 385/73 |
| 6,155,823 A | | 12/2000 | Nagel |
| 6,200,134 B1 | * | 3/2001 | Kovac et al. ................ 433/29 |
| 6,202,242 B1 | * | 3/2001 | Salmon et al. .............. 15/22.1 |
| 6,208,788 B1 | * | 3/2001 | Nosov ........................ 362/572 |
| 6,318,996 B1 | * | 11/2001 | Melikechi et al. ........... 433/29 |
| 6,325,623 B1 | * | 12/2001 | Melnyk et al. ............... 433/29 |
| 6,331,111 B1 | * | 12/2001 | Cao ........................... 433/29 |
| 6,361,489 B1 | | 3/2002 | Tsai |
| 6,555,958 B1 | * | 4/2003 | Srivastava et al. .......... 313/506 |
| 6,600,175 B1 | * | 7/2003 | Baretz et al. ............... 257/100 |
| 6,692,251 B1 | * | 2/2004 | Logan et al. ................ 433/29 |
| 2002/0147383 A1 | | 10/2002 | Weber et al. |
| 2003/0133203 A1 | * | 7/2003 | McLean et al. |
| 2003/0142413 A1 | * | 7/2003 | McLean et al. |
| 2003/0215766 A1 | * | 11/2003 | Fischer et al. |

* cited by examiner

Primary Examiner—Thomas M. Sember
Assistant Examiner—Ismael Negron
(74) Attorney, Agent, or Firm—Workman Nydegger

(57) ABSTRACT

A tissue illumination apparatus is useful in identifying caries, calculus, fractures, diseases or other defects in tissues within the oral cavity. The tissue illumination apparatus includes a light emitting device and at least one focusing lens. The lens may be configured to be integrally or releasably attached to the light emitting device. The tissue illumination apparatus may optionally include one or more intermediate focusing lenses. The fluorescing lens and/or any intermediate focusing lenses are made from any desired material that may be impregnated or coated with one or more fluorescing compounds and/or one or more light-absorbing dyes or pigments. The fluorescing lens converts light emitted by the light emitting device into light having a longer wavelength in order to transilluminate oral tissues and render certain dental tissues and/or defects therein visible to a dental practitioner.

61 Claims, 5 Drawing Sheets

ILLUMINATION APPARATUS HAVING A LIGHT-CONVERTING LENS FOR INCREASING VISUAL CONTRAST BETWEEN DIFFERENT ORAL TISSUES

BACKGROUND OF THE INVENTION

1. The Field of the Invention

The present invention is in the field of light emitting devices and, more particularly, devices used to illuminate oral tissues.

2. The Relevant Technology

In the dental industry, light emitting devices are sometimes used in the detection of caries, calculus, fissures, fractures, tarter, plaque, and other dental defects. They may also be used to diagnose soft tissue disorders. The component wavelengths of white light are either absorbed by or transmitted through the dental tissue. Healthy tissues generally allow certain wavelengths of light (typically longer wavelengths, such as red) to be transmitted through the tissue. This phenomenon is known as transillumination. Diseased tissue and other defects generally absorb these same wavelengths, causing a visual contrast between healthy and diseased tissue.

One type of light emitting device for dental diagnosis includes a light source, such as an incandescent bulb or a high intensity light emitting diode ("LED"), configured to emit white light. Such a light emitting device can be modified by attaching a filtering tip to reduce glare. For example, Ivoclar-Vivident provides a diagnostic device that emits white light connected to a green tinted filter for use in the visual identification of plaque. In some ways, however, simply filtering white light is inefficient since most of the light energy is filtered out and, hence, wasted.

In view of the foregoing, there is an ongoing need to provide improved tissue illuminating apparatus for diagnosing caries, calculus, fractures, fissures and other dental defects in teeth and/or diseased or otherwise abnormal soft oral tissue.

BRIEF SUMMARY OF THE INVENTION

The present invention is directed to a tissue illumination apparatus that can be used to enhance the visibility of oral tissues, such as teeth and soft oral tissues of the gums, tongue, lips or cheeks. The tissue illumination apparatus includes a light emitting device that emits a first spectrum of light and at least one lens connected to the light emitting device which converts at least a portion of the first spectrum of light into a second spectrum of light having a longer wavelength that enhances the visibility of defects in at least one type of oral tissue. The tissue illumination apparatus is useful for identifying caries, calculus, fractures, fissures or other defects in teeth and/or diseased or abnormal soft oral tissues.

The first spectrum of light emitted by the light emitting device can be monochromatic or fall within a range of wavelengths, as can the second spectrum of light transmitted or produced by the lens. In one embodiment, the light emitting device includes at least one LED or LED array that emits light within a defined spectral range (e.g., blue light capable of curing at least one light curable compound). In this embodiment, the lens is adapted so as to convert or shift the spectrum of light emitted by the one or more LEDs or LED arrays toward a longer wavelength. Because longer wavelengths (e.g., green, yellow, orange and/or red) are better able to penetrate, and therefore transilluminate certain tissues, compared to blue light, converting blue light into longer wavelength light enhances the ability of the light emitting device to render defects in oral tissues more visible.

In order to convert shorter wavelength light into longer wavelength light that is better able to illuminate defects in oral tissues, the lens is preferably impregnated with, coated or otherwise made using one or more fluorescing dyes, pigments or other compounds (e.g., fluorizine) that are able to absorb shorter wavelength light and then emit longer wavelength light. Two or more different fluorescing compounds can be used, e.g., mixed together or layered to get a blended effect or within different sections of the lens to yield outputs at different wavelengths. A plurality of lenses can be used interchangeably or in a stacked configuration. At least a portion of the lens can simply allow light to pass through unfocused or it can focus the light (e.g. to diffuse or collimate the light). At least a portion of the lens may include a light absorbing dye or pigment that filters all or some of the light emitted by the light emitting device and/or that would otherwise be transmitted by the lens (e.g., to filter out blue light not converted by the fluorescing compound into longer wavelength light).

The lens may be integrally or removably connected to the light emitting device. The type of connection between the lens and the light emitting device may include a snap fit, a compression fit, a friction fit, a threaded coupling, a bayonet coupling, adhesive, tape, or other couplings. The lens may be disposed next to the light source (e.g., an LED or incandescent bulb), or to a light guide (such as a fiber optic bundle light guide), interposed between the light source and the lens.

The lens can be made from any suitable material that transmits light (e.g., acrylic, polyacrylic, polypropylene, polycarbonate, silicone, aluminum dioxide, sapphire, quartz, or glass). A portion of the lens may optionally be coated with an opaque material in order to reduce the size of the footprint of light transmitted by the lens. The lens may or may not include features that focus (e.g., diffuse or collimate) light as desired.

A light emitting apparatus and one or more lenses having similar or different properties or features may be sold together as a kit. The kit may include a plurality of single-use lenses that are discarded after use for sanitation purposes. The kit may include a plurality of interchangeable lenses that can be selected based on the spectrum and/or footprint of light that one desires to transmit using one or more of the lenses.

In use, a tissue illumination apparatus comprising a light emitting device and one or more lenses is used to illuminate oral tissue in order to diagnose defects within such tissues and/or confirm that a patient's oral tissues are healthy. The light transmitted by the illumination apparatus can be directed to the front of a patient's teeth or oral tissues, or it may be directed to the back in order to illuminate the tissue (e.g., a tooth) from behind.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings, in which.

DETAILED DESCRIPTION OF THE PREFERRED EMBODIMENTS

Figure 1:
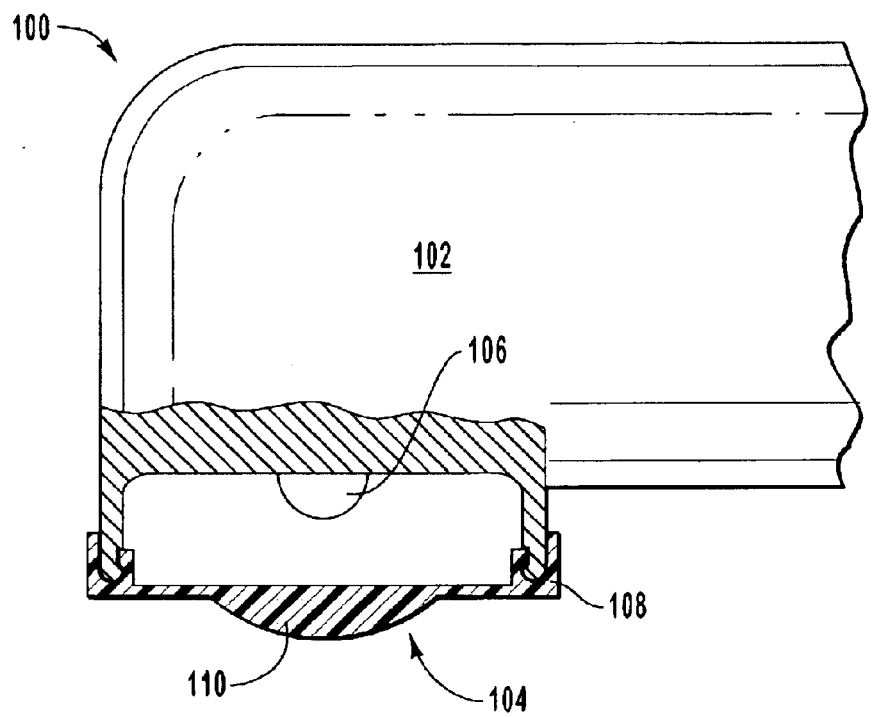
FIG. 1 depicts an exemplary tissue illumination apparatus according to the invention that includes a light emitting device and a fluorescing lens, a portion of which is adapted to focus light.

A detailed description of exemplary fluorescing lenses, tissue illumination apparatus, and kits and methods utilizing the foregoing, will now be provided with specific reference to drawings illustrating preferred embodiments of the invention. It will be appreciated that like structures will be provided with like reference designations. To provide context for interpreting the scope of the invention, certain terms used throughout the application will now be defined.

As used herein, the term "light emitting device" includes any dental light device that generates light, whether using a bulb, one or more LEDs, one or more LED arrays, or other light source. The term "light emitting device" also includes light guides (e.g., a fiber optic light guide) used to capture and transmit light emitted by a light source. The term "light source" refers to that portion of the "light emitting device" that actually generates and emits light.

The term "lens" refers to any structure that may be attached to a light emitting device through which light may travel (i.e., that is able to transmit at least a portion of the light emitted by the light emitting device). The term "lens" should be broadly interpreted so as to include lenses that are able to focus light and those that do not focus light.

The term "footprint," as used herein, refers to the cross-sectional shape of light emitted by a tissue illumination apparatus or other light emitting device. The dimensions of the footprint will typically vary according to the distance of the footprint from the light source and the angle at which the light is emitted by the light source. The general shape and dimensions of a footprint can generally be identified by placing a flat object in front of a light source and observing the area illuminated by the light source. The footprint of light emitted by a light emitting device can be altered by using a focusing lens (e.g., a diffusing or collimating lens).

The term "spectrum of light" refers to light that is monochromatic or substantially monochromatic, as well as light that falls within a range of wavelengths. The term "wavelength", when used in the context of the term "spectrum of light", refers to either the actual wavelength of monochromatic light or the dominant wavelength within a range of wavelengths.

In general, the present invention includes a tissue illumination apparatus that includes a light emitting device and at least one lens connected to the light emitting device that converts light emitted by the light emitting device into light having a longer wavelength. In the case of violet or blue light, for example, shifting the light to a longer wavelength (e.g., green, yellow, orange or red) increases the ability of the light to illuminate and make visible defects in at least one type of oral tissue. For example, the tissue illumination apparatus is useful in visually identifying one or more of caries, calculus, fractures, fissures or other defects in teeth and/or diseased or abnormal soft oral tissues. Attention will now be turned to the drawings, which depict several exemplary tissue illumination devices according to the invention as well as methods of using such devices.

FIG. 1 illustrates an exemplary tissue illumination apparatus 100 according to the present invention which includes a light emitting device 102 and a fluorescing lens 104 attached to the light emitting device 102. The light emitting device 102 includes a light source 106, such as a single bulb or light emitting diode (LED), which is adapted to emit a predetermined spectrum of light. In one embodiment, the spectrum of light emitted by the light source includes violet and blue light (approximately 375–525 nm, e.g., 410–490 nm) in order for the spectrum of light to be suitable for curing one or more different types of light-curable dental compositions. For brevity, a spectrum of light that includes both violet and blue components is often referred to simply as "blue light". A light emitting device that emits blue light is suitable as a dental curing light because it can be used to trigger the polymerization of various light curable dental compositions. It will be appreciated, however, that the spectrum of light emitted by the light source 106 may include light composed of any desired color or group of colors. The spectrum of light emitted by the light source 106 may be monochromatic or within a range of wavelengths.

In one embodiment, the light emitting device 102 may include one or more switches (e.g., buttons, not shown) for selective increasing or decreasing the intensity of light that is emitted by the light source. In connection with this, the light emitting device may also include an aural, visual, or tactile indication of the intensity of light being emitted by the light emitting device 102. For example, the light emitting device 102 may emit a sound having increasing pitch as the intensity of light increases and decreasing pitch as the intensity of light decreases.

The exemplary lens 104 includes one or more attachment structures 108 that aid in removably attaching the lens 104 to the light emitting device 102. The attachment structure 108 shown in FIG. 1 is a snap fit structure configured to mate with corresponding structure located on the light emitting device 102. It will be appreciated, however, that the attachment structure 108 can be modified to be provide any desired mode of attachment to the light emitting device 102 (e.g., a compression fit, a friction fit, a threaded coupling, a bayonet coupling, adhesive, tape, and the like). It will also be appreciated that the lens 104 may be integrally attached to the light emitting device 102.

Because of the orientation of the lens 104 relative to the light source 106, light energy emitted by the light emitting device 106 enters a side of the lens 104 proximal to the light source 106 and exits through the distal side. In this way, the lens 104 is able to transmit at least a portion of the light emitted by the light source 106.

The lens 104 also includes a focusing lens or portion 110 that is able to focus (e.g., collimate) light emitted by the light source 106. At least a portion of the light emitted by the light source 106 is captured by and passes through the focusing lens or portion 110. Some of the light may also pass through the remaining portion of the lens 104 depending on the angle at which light is emitted by the light source 106. It will be appreciated that the lens 104 can be altered so as to not include a focusing portion or lens 110, or so as to having multiple focusing lenses as desired.

In one embodiment, at least a portion of the lens 104 comprises at least one fluorescing dye, pigment or other compound that is able (or adapted) to convert at least a portion of the spectrum of light emitted by the light source 106 to an altered spectrum of light having a longer wavelength. The lens 104 may be impregnated, coated or otherwise made using one or more fluorescing dye compounds. Two or more different fluorescing compounds can be used, e.g., mixed together or layered within or on the lens 104 to get a blended effect or within different sections of the lens to yield different sections of transmitted light having different wavelengths.

In one embodiment, the lens 104 may comprise a first layer comprising a first fluorescing compound that converts at least a portion of the spectrum of light emitted by the light source 106 into a second spectrum of light and a second layer comprising a second fluorescing compound that converts the second spectrum of light and/or light that passes unaltered through the first layer into a third spectrum of light. In addition to, or instead of, the aforementioned multiple layers, different sections of the lens 104 may comprise different fluorescing dyes in order for the footprint of light transmitted by the lens 104 to have regions of varying wavelength.

In one embodiment, at least a portion of the lens 104 may include a light absorbing dye or pigment that filters all or some of the light emitted by the light emitting device and/or that would otherwise be transmitted by the lens. For example, the lens may include a light absorbing dye or pigment that filters out light emitted by the light source 106 that is not converted into longer wavelength light. For example, the one or more fluorescing compounds may only be able to effectively convert a fraction of the light emitted by the light source 106 into the altered spectrum of light, with some of the original spectrum of light passing through the lens 104 unchanged. Filtering the component of transmitted light that remains unaltered might assist the practitioner in better visualizing defects in the targeted tissue by, e.g., reducing glare that might otherwise be caused by the unaltered light. In one embodiment, the lens 104 comprises a first layer through which light passes comprising one or more fluorescing compounds and a second layer through which light subsequently passes comprising the light absorbing dye or pigment in order to filter light that remains unaltered after passing through the first layer.

In the case where the light source 106 emits ultraviolet light (approximately 300–400 nm), violet light (approximately 400–450 nm) and/or blue light (approximately 450–500 nm), the lens 104 may advantageously be adapted to convert such light into one or more of green light (approximately 500–550 nm), yellow light (approximately 550–600 nm), orange light (approximately 600–650 nm), or red light (approximately 650–700 nm). It is generally within the scope of the invention to provide a lens having a fluorescing compound that is able to convert any spectrum of light having a beginning wavelength into one or more spectra of light having other wavelengths that are longer than the beginning wavelength. The spectrum of light transmitted by the lens 104 may be monochromatic or within a range of wavelengths.

As a general rule, longer wavelengths of light are better able to illuminate and make visible certain oral tissues and/or defects contained therein. For example, green light has been found to be particularly useful in helping to detect the existence of plaque, calculus, tartar, or other impurities on the surface of a tooth. Yellow, orange and red light are particularly useful in detecting caries in a tooth, as well as diseases or other defects within soft oral tissues, such as soft tissues associate with a patient's gums, tongue or cheek. That is because longer wavelengths are better able to penetrate, and thereby transilluminate, healthy oral tissues. Defects typically block or scatter light in such a way as to make them more visible when surrounding healthy tissue is transilluminated.

The lens 104 may comprise any suitable material that is able to transmit light. A portion of the lens may also comprise a material that does not transmit light, and/or be coated with an opaque material, in order to reduce the size of the transmitted footprint of light. For example, the lens 104 may comprise or be manufactured using one or more of acrylic, polyacrylic, polypropylene, polycarbonate, silicone, aluminum dioxide, sapphire, quartz, glass, and the like. The lens 104 may be formed using any manufacturing process (e.g., molding, machining, or assembling).

One or more fluorescing compounds may be added to the material during manufacture of the lens 104, or else coated onto one or more surfaces of the lens 104. It is within the scope of the invention to utilize any fluorescing compound that alters light in a desired or suitable manner. An example of a class of fluorescing compound is fluorizine. A variety of fluorescing compounds sold under the trade name Edgeglo® are available from PolyOne Corporation. Examples of suitable Edgeglo® fluorescing colors include green, yellow, orange, and red.

Figure 2:
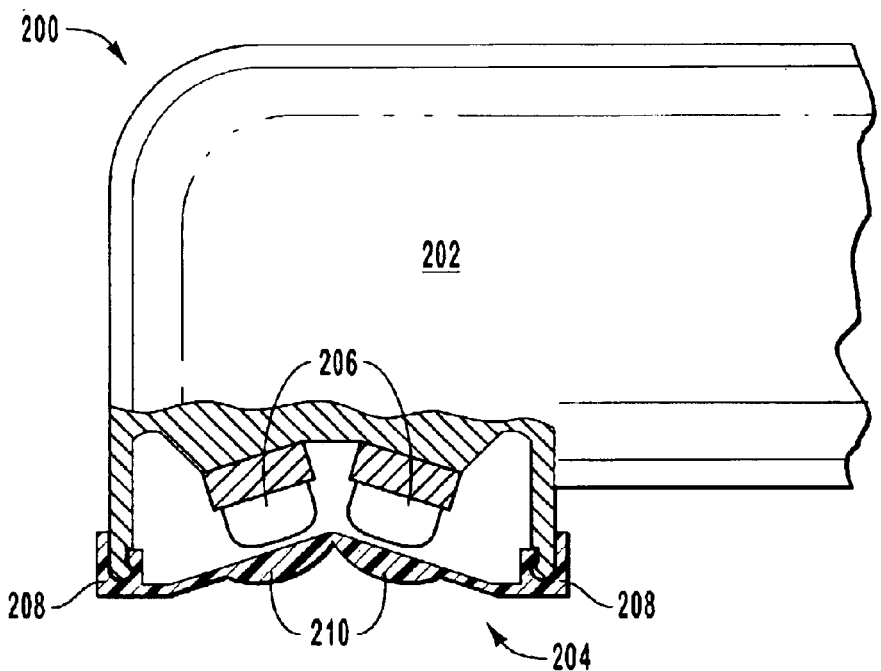
FIG. 2 depicts an exemplary tissue illumination apparatus according to the invention that includes a light emitting device having two LEDs and a fluorescing lens, a portion of which includes separate focusing lenses adapted to focus light emitted by the LEDs.

FIG. 2 illustrates an alternative exemplary embodiment of a tissue illumination apparatus 200 according to the invention, which includes a light emitting device 202 containing two LED light sources 206 and a lens 204 having a pair of focusing lenses 210 integrally formed therein. The lens 204 also includes one or more attachment structures 208 that aid in removably attaching the lens 204 to the light emitting device 202. The lens 204 may, however, be integrally attached to the light emitting device 202 or removably attached using other attachment structures (not shown), such as those discussed above.

In one embodiment, at least a portion of the lens 204 includes or is coated with one or more fluorescing compounds able to convert shorter wavelength light emitted by the light sources 206 into longer wavelength light more suitable for visually observing defects in oral tissue. In another embodiment, at least a portion of the lens 204 may include or be coated with one or more light-absorbing pigments or dyes that are able to absorb at least some wavelengths or components of light emitted by the light sources 206. The lens 204 can be modified to include any of the features discussed above relative to lens 104 of FIG. 1.

Because the light emitting device 202 includes two LEDs 206, it is possible to select LEDs that emit light of differing spectra. If so, the lens 204 may include one or more different fluorescing compounds selected specifically for converting the spectrum of light emitted by each LED. Additional LEDs that emit the same or additional spectra may be used, as can a lens 204 having additional regions comprising the same or differing fluorescing compounds.

Figure 3:
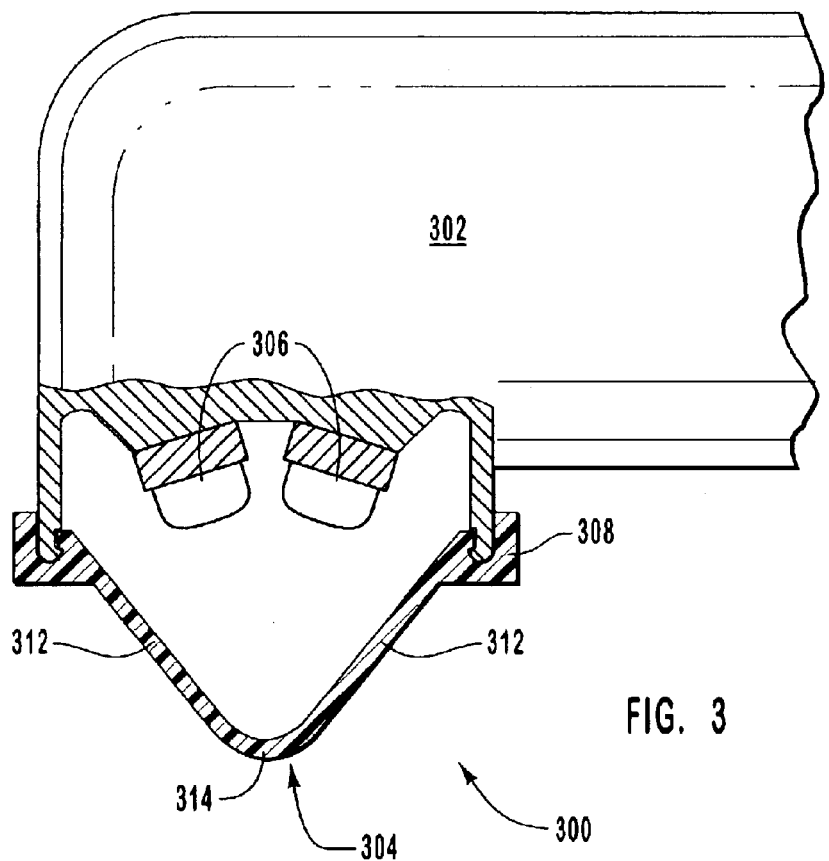
FIG. 3 depicts an exemplary tissue illumination apparatus according to the invention that includes a light emitting device and a non-focusing fluorescing lens having a conical shape.

FIG. 3 illustrates another exemplary embodiment of a tissue illumination apparatus 300 according to the invention, which includes a light emitting device 302 containing two LED light sources 306 and a conical lens 304. The conical lens 304 includes one or more attachment structures 308 that aid in removably attaching the lens 304 to the light emitting device 302. The conical lens 304 may, however, be integrally attached to the light emitting device 302 or removably attached using other attachment structures (not shown), such as those discussed above. The conical lens 304 includes a pair of angled sidewalls 312 that extend from at or near the attachment structures 308 and converge at an apex 314.

In one embodiment, at least a portion of the conical lens 304 includes or is coated with one or more fluorescing compounds able to convert shorter wavelength light emitted by the light sources 306 into longer wavelength light more suitable for visually observing defects in oral tissue. In another embodiment, at least a portion of the conical lens 304 may include or be coated with one or more light-absorbing pigments or dyes that are able to absorb at least some wavelengths or components of light emitted by the light sources 306. The conical lens 304 can be modified to include any of the features discussed above relative to lens 104 of FIG. 1 or lens 204 of FIG. 2.

Figure 4:
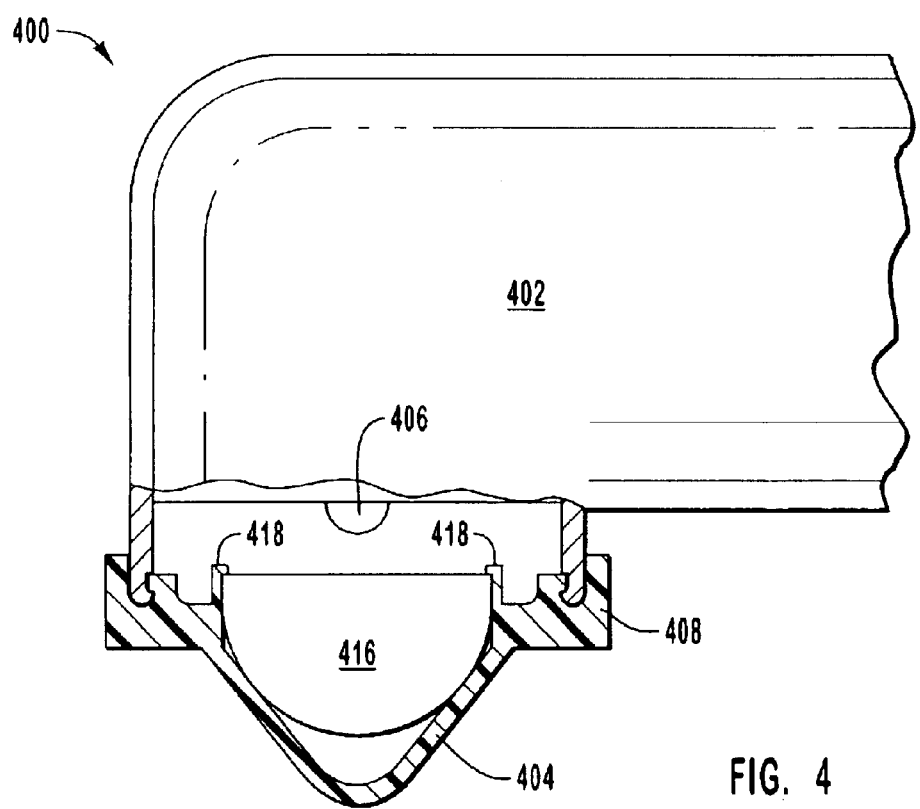
FIG. 4 depicts an exemplary tissue illumination apparatus according to the invention that includes a light emitting device, a non-focusing fluorescing lens having a conical shape, and an intermediate focusing lens interposed between a light source and the fluorescing lens.

FIG. 4 illustrates an exemplary embodiment of a tissue illumination apparatus 400 that includes a light emitting device 402, a conical lens 404, and a focusing lens 416. The light emitting device 402 includes a light source 406, such as a bulb, an LED or LED array. The conical lens 404 includes one or more attachment structures 408 that aid in removably attaching the lens 404 to the light emitting device 402. The conical lens 404 may, however, be integrally attached to the light emitting device 402 or removably attached using other attachment structures (not shown), such as those discussed above.

In one embodiment, at least a portion of the conical lens 404 includes or is coated with one or more fluorescing compounds able to convert shorter wavelength light emitted by the light sources 406 into longer wavelength light more suitable for visually observing defects in oral tissue. In another embodiment, at least a portion of the conical lens 404 may include or be coated with one or more light-absorbing pigments or dyes that are able to absorb at least some wavelengths or components of light emitted by the light source 406. The conical lens 404 may include any of the features discussed above relative to lens 104 of FIG. 1, lens 204 of FIG. 2, or lens 304 of FIG. 3. Because the focusing lens 416 may include one or more fluorescing compounds and/or one or more light-absorbing dyes or pigments, at least a portion of the conical lens 404 may be transparent so as to allow light to pass through unaltered.

The focusing lens 416 is interposed between the conical lens 404 and the light source 406 in order to capture and focus (e.g., collimate) at least a portion of the light emitted by the light source 406. The focusing lens 416 is shown with a hemispherical configuration; however, other configurations may be used depending on the desired footprint (e.g., aspheric, convex, concave, and the like). In this embodiment, the focusing lens 416 is attached to the conical lens 404 by means of one or more attachment structures 418. The focusing lens 416 may be transparent or else impregnated, coated or otherwise treated with one or more fluorescing compounds and/or one or more light-absorbing dyes or pigments as discussed above with respect to other lenses. In one embodiment, where the focusing lens 416 contains a fluorescing compound that alters the wavelength of at least some of the light energy emitted by the light source 406, the conical lens 404 may be impregnated, coated or otherwise treated with one or more light-absorbing dyes or pigments that filter out a portion of the spectrum of light transmitted by the focusing lens 416 (e.g., light emitted by the light source 406 that passes through the focusing lens 416 unaltered). The conical lens 404 may, of course, be transparent, as could the focusing lens 416, so long as the other component is able to convert light emitted by the light emitting device 402 into one or more spectra of light having a desired wavelength.

Figure 5:
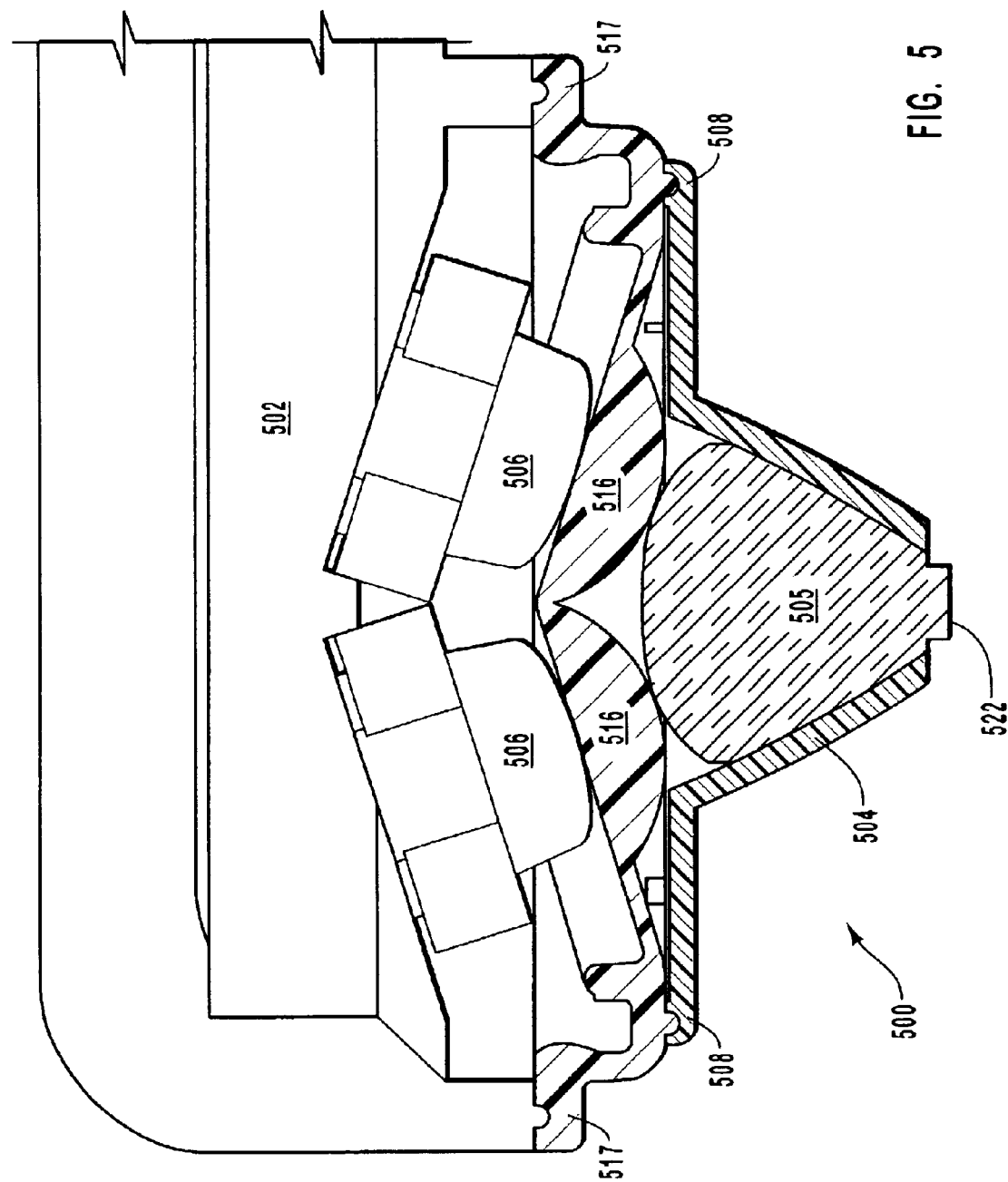
FIG. 5 depicts an exemplary tissue illumination apparatus according to the invention that includes a light emitting device, an outer lens having a conical shape and a hollow interior section, an inner lens disposed within the hollow interior section, and focusing lenses interposed between a light source and the inner lens.

FIG. 5 illustrates another exemplary embodiment of a tissue illuminating apparatus 500 according to the invention, which includes a light emitting device 502, an outer lens 504, an inner lens 505, and a pair of focusing lenses 516. The light emitting device 502 includes a pair of LED or LED array light sources 506. The focusing lenses 516 are integrally or removably attached to the light emitting device 502 by one or more attachment structures 517. The outer lens 504 is integrally or removably attached to the focusing lenses 516 by one or more attachment structures 508.

In one embodiment, at least a portion of the outer lens 504 includes or is coated with one or more fluorescing compounds able to convert shorter wavelength light emitted by the light sources 506 into longer wavelength light more suitable for visually observing defects in oral tissue. In another embodiment, at least a portion of the outer lens 504 may include or be coated with one or more light-absorbing pigments or dyes that are able to absorb at least some wavelengths or components of light emitted by the light source 506. The outer lens 504 can be modified to include any of the features discussed above relative to any of the lenses of FIGS. 1–4. Because either the focusing lenses 516 or inner lens 505 may include one or more fluorescing compounds and/or one or more light-absorbing dyes or pigments, at least a portion of the outer lens 504 may be transparent and allow light to pass through unaltered. In the alternative, because the outer lens 504 has an opening at an end thereof through light may pass unimpeded or unaltered by the outer lens 504, at least a portion of the outer lens 504 may be entirely opaque in order to reduce the size of the footprint of light passing through the outer lens 504.

The focusing lenses 516 are interposed between the outer lens 504 and the light sources 506 in order to capture and focus at least a portion of the light emitted by the light sources 506. In one embodiment, each focusing lens 516 captures and focuses at least a portion of the light emitted by a corresponding light source 506. The focusing lenses 516 may be transparent or else impregnated, coated or otherwise treated with one or more fluorescing compounds and/or one or more light-absorbing dyes or pigments in a manner discussed above with respect to the lenses of FIGS. 1–4. In one embodiment, where one or both of the focusing lenses 514 contain a fluorescing compound that alters the wavelength of at least some of the light energy emitted by the light sources 506, at least a portion of the outer lens 504 may be impregnated, coated or otherwise treated with one or more light-absorbing dyes or pigments that filter out a portion of the spectrum of light transmitted by the focusing lenses 516 (e.g., light emitted by the light sources 506 that passes through the focusing lenses 516 unaltered).

The inner lens 505 is disposed within an interior chamber or cavity defined by the outer lens 504. The inner lens 505 may be transparent or else impregnated, coated or otherwise treated with one or more fluorescing compounds and/or one or more light-absorbing dyes or pigments as discussed above with respect to other lenses. In one embodiment, where one or both of the focusing lenses 514 contain a fluorescing compound that alters the wavelength of at least some of the light energy emitted by the light sources 506, at least a portion of the inner lens 505 may be impregnated, coated or otherwise treated with one or more light-absorbing dyes or pigments that filter out a portion of the spectrum of light transmitted by the focusing lenses 516 (e.g., light emitted by the light sources 506 that passes through the focusing lenses 516 unaltered).

The inner lens 505 further includes a light emitting tip 520 adjacent to the opening or cavity at the end of the outer lens 504 through which at least of portion of the light that enters the inner lens 505 may exit. In the case where the outer lens 504 is opaque or otherwise blocks some or all of the light emitted by the light sources 506, the footprint of light that emerges from the outer lens will be defined by the size of the opening or cavity at the end of the outer lens 504. A small footprint of light may be useful in some situations because it reduces light energy output that might otherwise be overpowering so as to cause glare to the dental practitioner. The inner lens 505 may optionally comprises a flexible or resilient material in order to cushion the tissue illumination apparatus 500 if placed directly against oral tissue.

Various other lens designs may be used in conjunction with the present invention and be used as fluorescing transillumination lenses. Exemplary lenses are disclosed in U.S. application Ser. No. 10/044,346, filed Jan. 11, 2002, and entitled "Optical Lens Used to Focus LED Light"; U.S. application Ser. No. 10/068,397, filed Feb. 5, 2002, and entitled "Curing Light With Plurality of LEDs and Corresponding Lenses Configured to Focus Light"; and U.S. application Ser. No. 10/328,510, filed Dec. 23, 2002, and entitled "Cone-Shaped Lens Having Increased Forward Light Intensity and Kits Incorporating Such Lenses". For purposes of disclosing lens designs and light emitting devices within the scope of the present invention, each of the foregoing applications is incorporated herein by reference.

Figure 6:
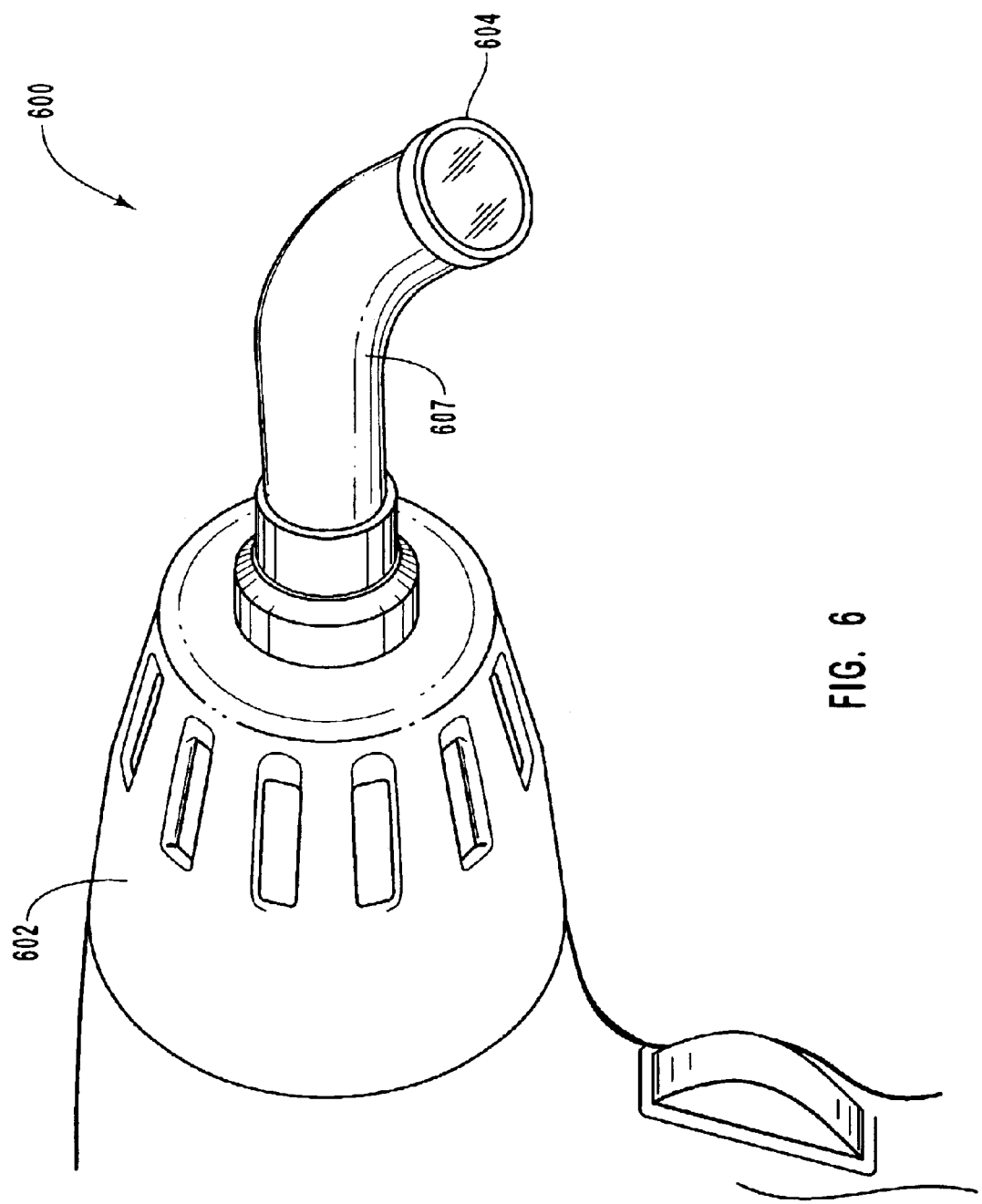
FIG. 6 depicts an exemplary tissue illumination apparatus according to the invention that includes a light emitting device, a fluorescing lens, and a fiber optic light guide interposed between a light source and the fluorescing lens.

FIG. 6 illustrates another exemplary embodiment of a tissue illuminating apparatus 600 according to the invention, which includes a light emitting device 602 having a light source (not shown) and a fiber optic light guide 603, and a lens 604 attached to the light guide 603. The light emitting device 602 may include any desired light source, such as a bulb, LED or LED array and, optionally, a cooling fan (not shown). The lens 604 may be integrally or removably attached to the light guide 603 and may include any of the lens features discussed above relative to FIGS. 1–5 or as described in the applications that have been incorporated by reference. As shown in FIG. 6, the lens 604 is substantially flat so that it does not appreciably focus light passing therethrough. This or any other tissue illuminating apparatus described herein can be altered by adding or removing lenses as desired to yield a tissue illuminating apparatus that emits light having desired properties. In addition, the lens 604 can be modified as desired to include any of the features discussed above relative to FIGS. 1–5.

Figure 7A:
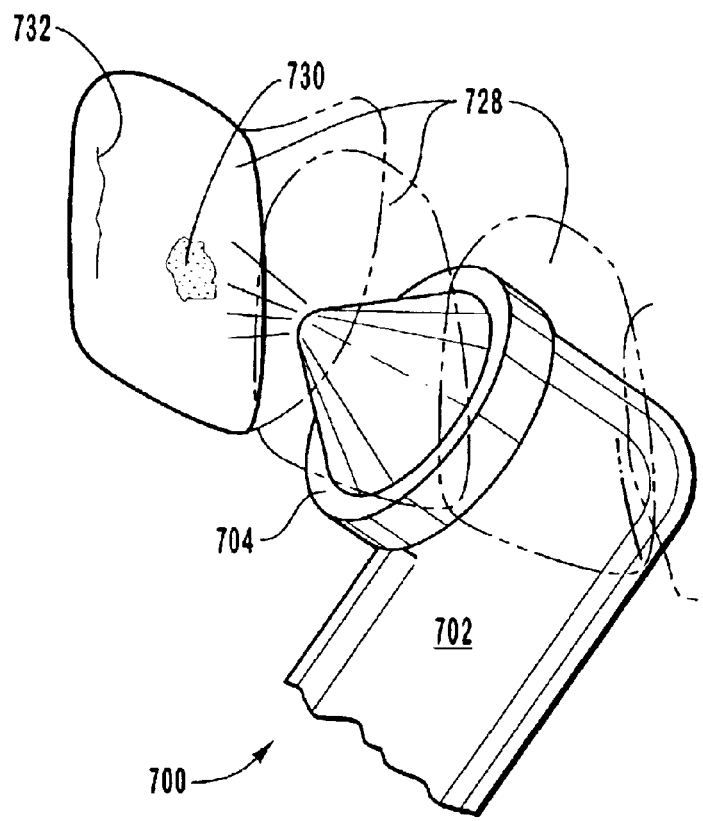
FIG. 7A illustrates the use of a tissue illumination apparatus according to the invention to identify caries and fractures within a tooth by illuminating the back side of the tooth.
Figure 7B:
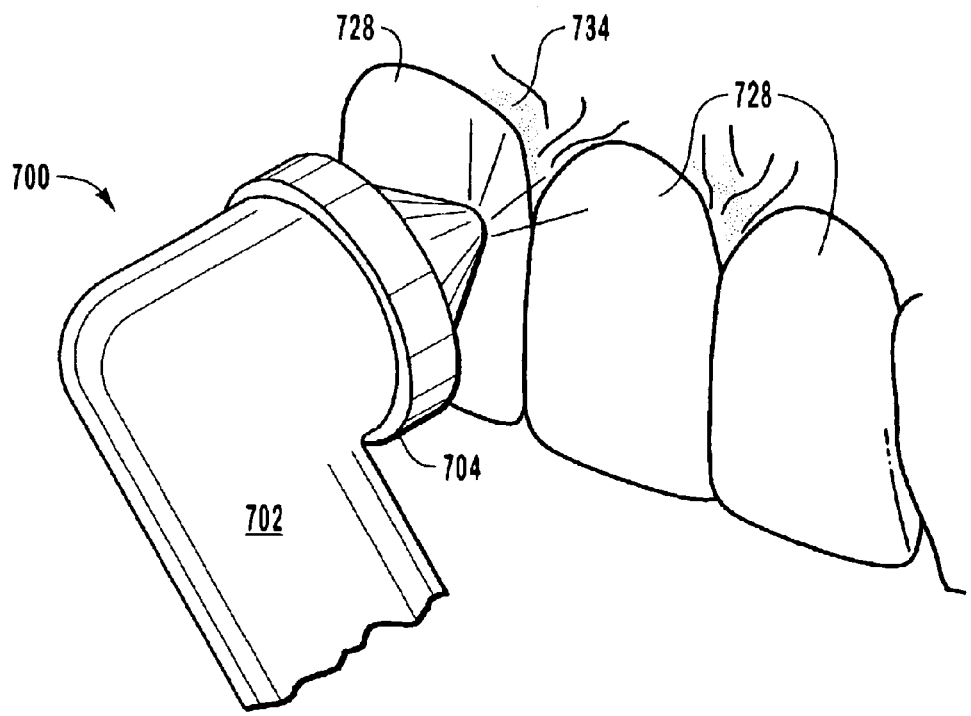
FIG. 7B illustrates the use of a tissue illumination apparatus according to the invention to identify diseased gingival tissue by illuminating the front side of the gums.

Use of an exemplary embodiment of a fluorescing transillumination lens is illustrated in FIGS. 7A and 7B. FIG. 7A more particularly shows a method of using a tissue illumination apparatus 700 according to the invention in which a fluorescing lens 704 attached to a light emitting device 702 is placed behind a tooth 728 in order to transilluminate the tooth and render caries 730 and/or a fissure 732 in the tooth 728 more visible. The fluorescing lens 704 converts light of a first spectrum emitted by the light emitting device 702 into a second spectrum of light having a wavelength that is longer than the first spectrum of light in order to enhance transillumination of the tooth 728. In this way, the tissue illumination apparatus 700 comprising the light emitting device 702 and fluorescing lens 704 better reveals the caries 730 and/or fissure 732 compared to the spectrum of light emitted by the light emitting device 702 that remains unaltered. The backlighting of oral tissue as illustrated in FIG. 7A may be useful in transilluminating other types of oral tissues and/or tooth maladies. For example, the tissue illumination apparatus 700 may be used to transilluminate other oral tissues in this manner such as gums, lips, or cheeks. It may also help a dental practitioner to identify various other tooth defects and abnormalities in this manner, such as plaque, tartar, calculus, loose fillings, and the like.

FIG. 7B more particularly shows a method of using the tissue illumination apparatus 700 in which the fluorescing lens 704 attached to the light emitting device 702 is placed in front of a tooth 728 and/or surrounding gingival tissue in order to illuminate or transilluminate the tooth and/or gingival tissue. The light that is transmitted by the fluorescing lens 704 renders a patch of diseased gingival tissue 734 more visible. The fluorescing lens 704 converts light of a first spectrum emitted by the light emitting device 702 into a second spectrum of light having a wavelength that is longer than the first spectrum of light in order to enhance transillumination of the tooth 728 and/or surrounding gingival tissue. In this way, the tissue illumination apparatus 700 comprising the light emitting device 702 and fluorescing lens 704 better reveals the diseased gingival tissue 734 compared to light emitted by the light emitting device 702 that remains unaltered. The front-lighting of oral tissue as illustrated in FIG. 7B may be useful in illuminating or transilluminating other types of oral tissues and/or tooth maladies. For example, the tissue illumination apparatus 700 may be used in this manner to illuminate or transilluminate a patient's lips and/or cheeks. It may also help a dental practitioner to identify various other tooth defects and abnormalities, such as plaque, tartar, calculus, loose fillings, and the like.

A light emitting device and one or more lenses having similar or different properties or features may be sold or otherwise provided together as a kit. The kit may include a plurality of single-use lenses that are discarded after use for sanitation purposes. The kit may include a plurality of interchangeable lens that can be selected based on the spectrum and/or footprint of light that one desires to transmit using one or more of the lenses. For example, kits according to the invention may include one or more light emitting devices and one or more of the lenses described herein.

The present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. An oral tissue illumination apparatus for increasing visual contrast between different oral tissues, comprising:

a light emitting device that emits a first spectrum of light having a first wavelength during use; and at least one lens connected to the light emitting device and positioned so that light emitted by said light emitting device passes through said lens during use, said lens converting at least a portion of the first spectrum of light to a second spectrum of light other than white light as the light passes through said lens during use, the second spectrum of light having a second wavelength that is longer than the first wavelength in order to enhance visual contrast between a first type of oral tissue and a second type of oral tissue when such tissues are simultaneously exposed to the second spectrum of light during use compared to visual contrast between such the tissues if simultaneously exposed to the first spectrum of light or white light.

2. A oral tissue illumination apparatus as recited in claim 1, wherein the first spectrum of light is substantially monochromatic.

3. An oral dental tissue illumination apparatus as recited in claim 1, wherein the second spectrum of light is substantially monochromatic.

4. An oral tissue illumination apparatus as recited in claim 1, wherein the first spectrum of light comprises a first range of wavelengths, with the first wavelength being a dominant wavelength within the first range of wavelengths.

5. An oral tissue illumination apparatus as recited in claim 1, wherein the second spectrum of light comprises a second range of wavelengths, with the second wavelength being a dominant wavelength within the second range of wavelengths.

6. An oral tissue illumination apparatus as recited in claim 1, wherein said lens is integrally connected to said light emitting device.

7. An oral tissue illumination apparatus as recited in claim 1, wherein said lens is removably connected to said light emitting device.

8. An oral tissue illumination apparatus as recited in claim 1, wherein said light emitting device further comprising a fiber optic light guide through which light emitted by a light source of said dental light emitting device passes before passing through said lens.

9. An oral tissue illumination apparatus as recited in claim 1, wherein said lens comprises at least one focusing lens that yields a desired footprint of light transmitted by said lens.

10. An oral tissue illumination apparatus as recited in claim 1, wherein said lens is a non-focusing lens.

11. An oral tissue illumination apparatus as recited in claim 1, wherein said lens comprises at least one of acrylic, polyacrylic, polypropylene, polycarbonate, silicone, aluminum dioxide, sapphire, quartz, or glass.

12. An oral tissue illumination apparatus as recited in claim 1, wherein said lens comprises at least one fluorizine compound.

13. An oral tissue illumination apparatus as recited in claim 1, wherein a portion of said lens is coated with an opaque material in order to reduce the size of the footprint of light transmitted by said lens.

14. An oral tissue illumination apparatus as recited in claim 1, wherein each of said first and second spectra of light are substantially monochromatic.

15. An oral tissue illumination apparatus as recited in claim 1, further comprising means for providing an aural indication of an intensity of light emitted from the oral tissue illumination apparatus.

16. An oral tissue illumination apparatus as recited in claim 1, further comprising means for providing a visual indication of an intensity of light emitted from the oral tissue illumination apparatus.

17. An oral tissue illumination apparatus as recited in claim 1, further comprising means for providing a tactile indication of an intensity of light emitted from the oral tissue illumination apparatus.

18. An oral tissue illumination apparatus as recited in claim 1, wherein said at least one lens includes at least two different sections having different fluorescing dyes, such that a footprint of light transmitted by the at least one lens has regions of varying wavelengths.

19. An oral tissue illumination apparatus as recited in claim 1, wherein said at least one lens includes at least two different lenses, at least one lens including light absorbing and filtering properties.

20. An oral tissue illumination apparatus as recited in claim 19, wherein said lens including light absorbing and filtering properties filters light in the first spectrum.

21. An oral tissue illumination apparatus as recited in claim 1, wherein said tissue illumination apparatus comprises a plurality of lenses, at least one of said plurality of lenses comprising at least one fluorescing compound that converts at least a portion of the first spectrum of light to the second spectrum of light.

22. An oral tissue illumination apparatus as recited in claim 21, wherein at least one other of said plurality of lenses comprises at least one other fluorescing compound that converts at least a portion of at least one of the first spectrum of light or second spectrum of light to a third spectrum of light having a third wavelength that is longer than the first and second wavelengths.

23. An oral tissue illumination apparatus as recited in claim 21, wherein at least one other of said plurality of lenses comprises at least one light-absorbing dye or pigment that filters out at least a portion of the first spectrum of light emitted by said light emitting device not converted into the second spectrum of light by said fluorescing compound.

24. An oral tissue illumination apparatus as recited in claim 1, wherein said light emitting device comprises at least one LED or LED array.

25. An oral tissue illumination apparatus as recited in claim 24, wherein said LED or LED array emits blue light suitable for curing at least one light curable dental composition.

26. An oral tissue illumination apparatus as recited in claim 25, wherein said LED or LED array emits wavelengths between about 375 nm and about 525 nm.

27. An oral tissue illumination apparatus as recited in claim 25, wherein said LED or LED array emits wavelengths between about 410 nm and about 490 nm.

28. An oral tissue illumination apparatus as recited in claim 24, wherein said lens contains at least one fluorescing compound so as to convert blue light to one of green light, yellow light, orange light, or red light.

29. An oral tissue illumination apparatus as recited in claim 28, wherein said lens comprises at least one fluorescing compound in a first layer and at least one other fluorescing compound in a second layer.

30. An oral tissue illumination apparatus as recited in claim 28, wherein said lens further comprises at least one light-absorbing dye or pigment that filters out at least a portion of the blue light emitted by said light emitting device not converted by said fluorescing compound to one of green light, red light, orange light, or yellow light.

31. An oral tissue illumination apparatus as recited in claim 30, wherein said at least one fluorescing compound is in a first layer and said at least one light-absorbing dye or pigment is in a second layer, said lens being oriented relative to said light emitting device so that light emitted by said light emitting device passes through said second layer subsequent to passing through said first layer.

32. An oral tissue illumination apparatus for identifying tooth defects and/or diseased or abnormal oral tissues, comprising:
    a light emitting device comprising at least one LED or LED array that emits a first spectrum of light having a first wavelength during use; and
    at least one lens that comprises at least one fluorescing compound and that is positioned relative to said light emitting device in order for light emitted by said light emitting device to pass through said lens after being emitted by said LED or LED array during use,
        said lens converting at least a portion of the first spectrum of light to a second spectrum of light other than white as the light passes through the lens during use,
        the second spectrum of light having a second wavelength that is longer than the first wavelength in order to enhance visual contact between healthy tissue and one or more of a tooth defect, diseased oral tissue, or abnormal oral tissue when such tissues are simultaneously exposed to the second spectrum of light during use compared to visual contrast between such tissues if simultaneously exposed to the first spectrum of light or white light.

33. A oral tissue illumination apparatus as recited in claim 32, wherein the lens is physically separated from said LED or LED array.

34. An oral tissue illumination apparatus as recited in claim 32, wherein the lens is detachable from said LED or LED array.

35. An oral tissue illumination apparatus as recited in claim 32, wherein each of said first and second spectra of light are substantially monochromatic.

36. A fluorescing tissue transillumination diagnostic lens that is connectable to a dental curing light in order to assist in diagnosing tooth defects and/or diseased or abnormal oral tissues by enhancing visual contrast between diseased and healthy oral tissues, comprising:
    a lens body comprising at least one fluorescing compound that converts a first spectrum of light having a first wavelength emitted by a dental curing light that passes through said lens body to a second spectrum of light other than white having a second wavelength that us longer than the first wavelength in order to enhance visual contrast between a first type of oral tissue and a second type of oral tissue when such tissues are simultaneously exposed to the second spectrum of light during use compared to visual contrast between such tissues if simultaneously exposed to the first spectrum of light or white light; and
    one or more attachment structures that removably attach said lens body to a dental curing light.

37. A fluorescing tissue transillumination diagnostic lens as defined in claim 36, wherein said at least one fluorescing compound converts blue light into at least one of green light, yellow light, orange light, or red light.

38. A fluorescing tissue transillumination diagnostic lens as recited in claim 36, wherein said lens body comprises at least one fluorescing compound in a first layer and at least one other fluorescing compound in a second layer.

39. A fluorescing tissue transillumination diagnostic lens as recited in claim 36, wherein said lens body further comprises at least one light-absorbing dye or pigment that filters out at least a portion of blue light emitted by a dental curing light not converted by said fluorescing compound to least one of green light, red light, orange light, or yellow light.

40. A fluorescing tissue transillumination diagnostic lens as recited in claim 39, wherein said at least one fluorescing compound is in a first layer and said at least one light-absorbing dye or pigment is in a second layer, said lens body being oriented so that light emitted by a dental curing light passes through said second layer subsequent to passing through said first layer.

41. An oral tissue illumination kit for use in increasing visual contrast between different oral tissues, comprising:
    a light emitting device that emits a first spectrum of light having a first wavelength during use;
    a first lens that is selectively attachable to and detachable from the light emitting device and that is positionable so that light emitted by said light emitting device passes through said first lens during use;
        said first lens converting at least a portion of the first spectrum of light to a second spectrum of light other than white light during use in order to enhance visual contrast between two different types of oral tissues when such tissues are simultaneously exposed to the second spectrum of light compared to if such tissues were simultaneously exposed to the first spectrum of light or white light; and
    a second lens that is selectively attachable to and detachable from the light emitting device and that is positionable so that light emitted by said light emitting device passes through said second lens during use,
        said second lens converting at least a portion of the first spectrum of light to a third spectrum of light other than white light during use in order to enhance visual contrast between two other different types of oral tissues when such tissues are simultaneously exposed to the third spectrum of light compared to if such tissues were simultaneously exposed to the first spectrum of light or white light.

42. An oral tissue illumination kit as recited in claim 41, wherein said dental curing light emits blue light.

43. An oral tissue illumination kit as recited in claim 41, wherein said kit further comprises a third lens that is selectively attachable and detachable from the light emitting device and that is positionable so that light emitted by said light emitting device passes through said third lens during use, said third lens converting at least a portion of the first spectrum of light to a fourth spectrum of light other than white light during use in order to enhance visual contrast between two other different types of oral tissues when such tissues are simultaneously exposed to the fourth spectrum of light compared to if such tissues were simultaneously exposed to the first spectrum of light or white light.

44. An oral tissue illumination kit as recited in claim 41, wherein at least one of said first or second lenses converts blue light into one of green light, yellow light, orange light, or red light.

45. An oral tissue illumination kit as recited in claim 41, wherein at least one of said first or second lenses better enhances visual contrast between healthy tissue and dental plaque compared to visual contrast between healthy tissue and plaque if simultaneously exposed to the first spectrum of light emitted by the dental curing light or white light.

46. An oral tissue illumination kit as recited in claim 41, wherein at least one of said first or second lenses better enhances visual contrast between healthy tissue and defects or variations in a tooth compared to visual contrast between healthy tissue and defects or variations in a tooth if simultaneously exposed to the first spectrum of light emitted by the dental curing light or white light.

47. An oral tissue illumination kit as recited in claim 41, wherein at least one of said first or second lenses better enhances visual contrast between healthy tissue and defects or variations in gingival tissue compared to visual contrast between such tissues if simultaneously exposed to the first spectrum of light emitted by the dental curing light or white light.

48. An oral tissue illumination kit as recited in claim 41, wherein each of said first, second and third spectra of light are substantially monochromatic.

49. A method for increasing visual contrast between different oral tissues, comprising:
    emitting a first spectrum of light from a dental curing device;
    converting said first spectrum of light into a second spectrum of light other than white that enhances visual contrast between healthy oral tissue and tooth defects and/or diseased or abnormal oral tissue when such tissues are simultaneously exposed to the second spectrum of light during use compared to visual contrast between such tissues if simultaneously exposed to the first spectrum of light or white light;
    simultaneously exposing such tissues to the second spectrum of light so as to enhance visual contrast between the healthy oral tissue and any tooth defects and/or diseased or abnormal oral tissue; and
    determining whether any tooth defects and/or diseased or abnormal oral tissue is present.

50. A method as recited in claim 49, further comprising filtering out at least a portion of said first spectrum of light not converted into said second spectrum of light.

51. A method as recited in claim 49, wherein converting said first spectrum of light into a second spectrum of light is performed by passing the light, having the first spectrum, through a lens attached to the dental curing device.

52. A method as recited in claim 49, further comprising placing the light curing device proximate to oral tissue and directing the light emitting from the light curing device to the oral tissue.

53. A method as recited in claim 49, wherein the light curing device comprises an LED light source.

54. A method as recited in claim 49, wherein each of said first and second spectra of light are substantially monochromatic.

55. A method as recited in claim 49, further comprising: providing an aural indication of an intensity of light emitted from the oral tissue illumination apparatus.

56. A method as recited in claim 49, further comprising: providing a visual indication of an intensity of light emitted from the oral tissue illumination apparatus.

57. A method as recited in claim 49, further comprising: providing a tactile indication of an intensity of light emitted from the oral tissue illumination apparatus.

58. A method as recited in claim 49, wherein said dental curing light emits blue light, the method comprising converting said blue light to at least one of green light, yellow light, orange light, or red light.

59. A method as recited in claim 58, the method comprising enhancing visual contrast between healthy oral tissue and dental plaque using green light.

60. A method as recited in claim 58, the method comprising enhancing visual contrast between healthy oral tissue and defects or variations in a tooth using at least one of red light, orange light, or yellow light.

61. A method as recited in claim 58, the method comprising enhancing visual contrast between healthy oral tissue and defects or variations in gingival tissue using at least one of red light, orange light, or yellow light.

* * * * *

UNITED STATES PATENT AND TRADEMARK OFFICE
CERTIFICATE OF CORRECTION

PATENT NO.    : 6,957,907 B2
DATED         : October 25, 2005
INVENTOR(S)   : Dan E. Fischer and Vasiliy Nosov It is certified that error appears in the above-identified patent and that said Letters Patent is hereby corrected as shown below:

<u>Title page,</u>
Item [75], Inventors, "Vasiliy Norsov, Sandy, UT (US)" to -- Vasiliy Norsov, Moscow, RUSSIAN FEDERATION --.

<u>Column 5,</u>
Line 27, change "having" to -- have --.

<u>Column 8,</u>
Line 58, before "light" insert -- which --.

<u>Column 9,</u>
Line 6, change "514" to -- 516 --.
Lines 60, 61 and 65, change "603" to -- 607 --.

<u>Column 10,</u>
Line 63, change "lens" to -- lenses --.

<u>Column 11,</u>
Line 52, change "comprising" to -- comprises --.

<u>Column 13,</u>
Line 60, change "that us" to -- that is --.

<u>Column 14,</u>
Line 14, after "compound to" insert -- at --.

Signed and Sealed this

Thirteenth Day of June, 2006

JON W. DUDAS
*Director of the United States Patent and Trademark Office*